United States Patent
Jang et al.

[11] Patent Number: 6,115,449
[45] Date of Patent: Sep. 5, 2000

[54] APPARATUS FOR QUANTITATIVE STEREOSCOPIC RADIOGRAPHY

[75] Inventors: Bor Z. Jang; Wen-Chiang Huang, both of Auburn, Ala.

[73] Assignee: Nanotek Instruments, Inc., Opelika, Ala.

[21] Appl. No.: 09/169,478

[22] Filed: Oct. 10, 1998

[51] Int. Cl.[7] ................................................. H01N 5/32
[52] U.S. Cl. ........................... 378/41; 378/42; 378/98.2; 348/51
[58] Field of Search ............................. 378/41, 42, 98.2; 348/51, 52, 53

[56] References Cited

U.S. PATENT DOCUMENTS

| | | |
|---|---|---|
| 1,447,399 | 3/1923 | Pease . |
| 1,992,894 | 2/1935 | Wantz . |
| 2,029,300 | 2/1936 | Arfsten . |
| 2,046,543 | 7/1936 | Boldingh . |
| 2,208,215 | 7/1940 | Gonzalez-Rincones . |
| 2,468,963 | 5/1949 | Dudley . |
| 2,511,097 | 6/1950 | Bonnet . |
| 2,518,884 | 8/1950 | Guentner et al. . |
| 2,521,154 | 9/1950 | Dudley . |
| 2,712,608 | 7/1955 | Atwell . |
| 3,004,159 | 10/1961 | Brancaccio . |
| 3,244,878 | 4/1966 | Stein et al. . |
| 3,382,362 | 5/1968 | Tokuyama et al. . |
| 3,560,740 | 2/1971 | Tripp ............................................ 250/61 |
| 3,671,745 | 6/1972 | Fouquart ..................................... 250/61 |
| 3,783,282 | 1/1974 | Hoppenstein ............................. 250/313 |
| 3,984,684 | 10/1976 | Winnek ..................................... 250/313 |
| 4,214,267 | 7/1980 | Roese et al. .............................. 358/111 |
| 4,696,022 | 9/1987 | Sashin et al. ............................... 378/41 |
| 4,737,972 | 4/1988 | Schoolman ................................. 378/41 |
| 4,769,701 | 9/1988 | Sklebitz ..................................... 358/111 |
| 4,819,255 | 4/1989 | Sato ........................................... 378/42 |
| 5,073,914 | 12/1991 | Asahina et al. ............................ 378/42 |
| 5,090,038 | 2/1992 | Asahina ...................................... 378/41 |
| 5,155,750 | 10/1992 | Klynn et al. ............................... 378/42 |
| 5,233,639 | 8/1993 | Marks ......................................... 378/41 |
| 5,493,595 | 2/1996 | Schoolman ................................. 378/41 |
| 5,818,064 | 10/1998 | Kohgami et al. .......................... 378/41 |
| 6,031,565 | 2/2000 | Getty et al. ................................ 348/51 |

OTHER PUBLICATIONS

F.H. Liu et al, "Design and Test of a Stereoscopic X–Radiographic Observing & Measuring Instrument" International J. Pressure Vessels & Piping vol. 44 (1990) 353–364.

F.H. Liu, et al. "3–D Flow Detection for the Welded Seams of Pressure Vessels", International J. Pressure Vessels & Piping vol. 48 (1991) 331–341.

*Primary Examiner*—David P. Porta
*Assistant Examiner*—Drew A. Dunn

[57] ABSTRACT

Apparatus for stereoscopically displaying radiographic images of the internal structure of an object and determining the spatial coordinates of a defect image inside the object, comprising: (a) two image display devices; (b) a secondary platform to support one of the two display devices with this platform being provided with horizontal movement means along with displacement sensor means; (c) a primary platform to support both image display devices; the primary platform being provided with movement means to horizontally slide both image display devices concurrently and the movement means being equipped with displacement-measuring means; (d) a sturdy base to support both platforms; (e) two reference lines being transversely aligned across and over the images; and (f) an observing assembly comprising two distinct and separate optical paths with each optical path being composed of properly arranged mirrors and lenses to direct the desired image into the respective observing eye. The optical paths are housed and protected by a casing means which is supported by a supporting member and provided with drive means to move the optical paths transversely; this supporting member being further supported by a sturdy base.

10 Claims, 14 Drawing Sheets

APPARATUS FOR QUANTITATIVE STEREOSCOPIC RADIOGRAPHY

FIELD OF THE INVENTION

The present invention relates to improved stereo spectroscopic radiography apparatus and, more particularly, to apparatus for stereoscopically displaying radiographic images and quantitatively assessing the internal feature positions of an object.

BACKGROUND OF THE INVENTION

High-energy radiations such as X-rays, gamma rays and neutrons are commonly used for non-destructive evaluation (NDE) of the internal defects of an object or for examination of the anomalies inside a human body. Radiographic images for either industrial NDE or medical applications can be obtained by radiography-on-film, fluoroscopy, and tomography methods. Each method has its advantages and disadvantages for a specific application.

Film radiography involves producing a sharp, natural size, permanent image of the internal features such as flaws or anomalies in an object. Such an image is usually not difficult to interpret. However, film radiography is often relatively slow and expensive. Silver emulsion film processing requires the utilization of chemicals that are eventually discarded, potentially creating environmental hazards.

Fluoroscopy or radioscopy entails the conversion of X-ray intensities into light intensities by utilizing a fluorescent screen. By placing the screen in the X-ray beam behind the specimen, one can produce an image of the specimen on the screen. The high X-ray absorbing capability of selected materials could result in low brightness images and hence poor sensitivity. One method to improve the fluoroscopic performance is to use a closed-circuit television (CCTV) camera to transfer the image on the fluorescent conversion screen on to a display monitor, relying on the electronic circuitry to enhance the signal and produce a bright image. Another technique is to use an image intensifier tube to convert X-rays into photons, which are then picked up by an image sensor. Commonly used image sensors are tube type TV cameras such as isocon, vidicons, and solid state charge coupled device (CCD) cameras. Another type of image sensor is the linear diode array (LDA), which can digitize and store the image to be viewed on a TV monitor. The digitization of the television signal has allowed a computer to be built into the system, and this advancement in computed radiography (CR) has greatly improved the attainable image quality. This development has also made it possible to perform real-time radiography.

Both the conventional film radiography and fluoroscopy only provide a two-dimensional (2-D) view of an object. In industrial applications, a 2-D image does not give a NDE technician an adequate perspective view on the spatial distribution of multiple flaws in a structural component, nor does it allow the technician to determine the depth of a particular flaw. For medical uses, a 2-D image may not provide a diagnostician adequate information as to the extent of a particular disorder, such as the exact depth of a foreign object in a human body.

To overcome some of the drawbacks of 2-D radiography, the approach of tomography was developed. Computed tomography (CT) involves obtaining and stacking a sequence of images representing 2-D cross sections or "slices" of the object. The 2-D images are acquired by rotating a thin, fan shaped beam of X-ray about the long axis of the object. X-ray attenuation measurements are obtained from many different directions across each slice. The 2-D images are reconstructed from these data through a sophisticated mathematical convolution and back projection procedure. A major drawback of tomography is that a NDE technician or diagnostician must mentally "stack" an entire series of 2-D slices in order to infer the structure of a 3-D object. The interpretation of a series of stacked 2-D images by an observer requires a great deal of specialized knowledge and skill. Further, such an approach is extremely time consuming and is prone to inaccuracy. The market price of a CT system typically exceeds a million U.S. dollars and, therefore, only select large hospitals or highly specialized governmental or industrial facilities could afford to have a CT system. Clearly, a need exists to develop a more affordable stereography system for 3-D inspection of the internal structure of an object.

Three-dimensional (3-D) or stereoscopic viewing provides a means for showing actual, more understandable spatial relationships among various features or flaws inside a body. Stereoscopic radiology was first introduced near the turn of the century, e.g. L. W. Pease, U.S. Pat. No. 1,447,399 (1923). Extensive patent and open literature can be found that describes the methods or apparatus for producing stereoscopic radiographs. U.S. Pat. No. 5,233,639 (1993), issued to Marks, summarized the pros and cons of various stereoscopic radiography methods, including stereo film radiography and stereoscopic fluoroscopy.

Most of the techniques that have been used to achieve the stereo effect is based on the theory of parallax. Specifically, an image recorded from the perspective of the right eye must be seen by the right eye while an image recorded from the perspective of the left eye must be seen by the left eye. A simple way to accomplish this is to provide distinct and separate optical paths to each eye from each recorded image. For instance, the right and left eye image pairs may be recorded as transparencies which, when inserted in a common hand-held 3-D viewer, are presented to each eye separately through magnifying lenses. A second example using the principle of distinct and separate optical paths is the mirror based viewer system. In this system, the image pairs are positioned under a viewer which, through two pairs of angled mirrors, directs each image to its corresponding observing eye. These conventional 3-D viewers, normally without proper markers or references, do provide the observer a 3-D perspective. However, they do not readily permit determination of the specific depths in which certain features (or flaws) are located relative to a predetermined reference.

Disclosed in U.S. Pat. No. 3,984,684 (1976) is a technique that allows both production of the stereo effect and measurements of the depth and size of one or more internal parts of an object. The technique entails successively directing the X-ray beams from an X-ray tube through the object, then through a parallax grating, and finally onto the film, The grating is mounted on the film support system. The object and the film support system together are translated in parallel paths laterally with respect to the beam path at different speeds. These speeds are such that the film and the object are maintained in congruent alignment with the X-ray tube. The grating moves slightly out of congruency causing the beam passing through the grating to slightly scan the film during the transverse. Also, the angle at which the object is exposed to radiation from the X-ray tube gradually changes. The film image contains a series of side-by-side variable aspect views or images of the object, corresponding in number to the number of slits in the grating. These images when viewed with a lenticular screen produce a 3-D perception. This technique requires the utilization of a complicated radiograph-taking system and a lenticular screen as described above. The stringent congruent alignment requirement has made this technique not readily adaptable to existing X-ray radiography apparatus.

Liu and co-workers (International Journal of Pressure Vessels & Piping, Vol.44, 1990, pp.353–364 and Vol.48, 1991, pp.331–341) have proposed a quantitative stereoscopic method which not only provides a 3-D perspective view of the internal features but permits convenient calculations of the coordinates (X,Y,Z) of one or more flaws inside an object. The method begins with taking a pair of radiograph films with the X-ray tube shifted laterally in a plane parallel to the film between the two exposures (while the object remains stationary). Alternatively, the same result can be achieved by shifting the object laterally while the X-ray source remains fixed. These radiograph films are then examined in a stereoscopic viewer. With suitable markers placed on the specimen surfaces when the radiographic films are being exposed, the position of a defect image inside the specimen can be determined. Hitherto, very few industrial stereo radiographs have yielded very good results possibly because of the lack of reference detail and the incapability of the conventional stereoscopes in coping with films of the density used in industrial radiology. The method proposed by Liu, et al. provides a sound basis upon which more effective stereoscopes for quantitative radiography can be designed. This method, however, has been limited to film radiography. What is clearly needed is improved apparatus, which are based on improved versions of Liu's principle and the various positive attributes of fluoroscopy, for conducting quantitative stereo radiology. The present invention provides apparatus for meeting this quantitative stereoscopic radiology need. The present invention application represents the second part of a pending U.S. patent (application Ser. No. 08/712.102 filed on Sep. 11, 1996 now abandoned), which was suggested to be divided up into two patents. Following such an suggestion, the first part, entitled "QUANTITATIVE STEREOSCOPIC RADIOGRAPHY METHODS", was submitted on Sep. 18, 1997.

OBJECTS OF THE INVENTION

The principal objects of the present invention are:

(1) to provide an improved apparatus of stereoscopically displaying radiography images and allow for more convenient and accurate determination of the location of an internal feature.

(2) to provide stereoscopic radiology apparatus for stereoscopic viewing of X-ray irradiated objects.

(3) to provide apparatus for not only stereoscopic viewing of the internal defects of an object but quantitative determination of the location, in precise (X,Y,Z) coordinates, of one or more defects inside an object.

(4) to provide apparatus for not only stereoscopic viewing of the internal features of an object through radiographic films but also quantitative determination of the location of a defect inside an object.

(5) to provide apparatus for not only stereoscopic viewing of the internal features of an object through radiographic films but also quantitative determination of the location of a defect inside an object; the apparatus are also capable of digitally displaying the spatial coordinates of the defect on a display device such as a liquid crystal display and a computer monitor.

(6) to provide apparatus for stereoscopic viewing of radiographic images displayed on TV or computer monitor screens and for determining the location of an internal feature;

(7) to provide such apparatus which are adaptable to industrial NDE or medical uses.

SUMMARY OF THE INVENTION

The present invention provides apparatus for conducting improved quantitative stereoscopic radiography. These apparatus work on either the improved version of the above-mentioned Liu's method of stereo film radiology or on integrating such a method with the great electronic imaging capabilities commonly associated with fluoroscopy.

Specifically, in one preferred embodiment, an apparatus is disclosed which provides capabilities of displaying a pair of radiographic images on the corresponding right and left video display devices of a stereoscopic viewing system. The pair of images can be obtained by transferring (e.g., scanning or digitizing) the corresponding radiography transparencies (negatives) onto one cathode ray tube (CRT), or two separate CRT monitors by using an image scanner or TV camera. Alternatively, the images can be obtained by directly using common fluoroscopy devices to display the images with out going through the intermediate film-taking procedure. This can be accomplished by directing the beam of an X-ray source (or other types of high energy radiation) through an object and by using an image intensifier to convert the radiation into visible light, allowing the image to be shown on a fluorescent screen. Alternatively, the light photons emitted from the image intensifier may be recorded by an image sensor which delivers the images either directly to video display devices or to an image storage device. In the latter case, the images will be later played back to the video display devices for examination.

Referring to FIG. 1a, both the right and left video display devices are each provided with a vertical reference line, which can be simply a thin opaque wire positioned vertically (herein referred to as transversely, or in the Y-coordinate direction) above and in front of the display screen. These wires shall remain stationary when radiographic images are being shifted. More preferably, these thin wires are attached transversely to the proximal ends (closer to the images) of the corresponding optical paths of an optical observing unit (FIG. 1c). Proper movement means are provided to allow the two images to be shifted laterally (horizontally, in the X-coordinate direction) either simultaneously in congruency or with respect to each other. Provisions are also given to record these shift distances. Shifting of the two images can be accomplished by positioning the two display devices on a slidable platform (e.g., a stage or table on a linear motion device), hereinafter referred to as the primary platform, and then horizontally translating this platform. Either the left or the right display device is also supported on a secondary platform which is capable of moving horizontally, independent from the movement of the primary platform. The secondary platform is slidably attached to the top surface of the primary platform. The movements of both platforms can be recorded by any movement measuring means such as a micrometer, sliding caliper, optical encoder, or any other displacement sensor. These movement measuring means are used to measure out the shift distances of both marker and defect images.

It may be noted that, referring to FIG. 1A–1C, the X-coordinate direction is the X-ray source shifting direction (when the radiography image is taken), which is also parallel to the platform movement direction and substantially parallel to the geometric line connecting both eyes of an operator. The transverse direction on the image plane is the Y-coordinate direction, which is the vertical direction in FIG. 1. The Z-coordinate direction is perpendicular to both the X-direction and Y-direction; i.e. being normal to the image plane and approximately in the sample depth direction.

In another embodiment, the pair of radiography images may be shown side by side on the same display unit, such as a TV monitor or a computer monitor. The monitor screen is artificially divided into two zones: a left zone showing the image to be presented to the left eye and a right zone showing the image to be presented to the right eye of an observer. There exist commercially available image processing software-hardware packages that are capable of providing and measuring the concurrent and separate movements of the two images on the screen. In yet another embodiment, the monitor is mounted on a horizontally slidable primary platform, which provides simultaneous shifting of the two images. Shifting of one image with respect to the other can be executed on the monitor by a simple computer command.

The two images can be viewed by an optical observing unit which is composed of two optical paths, one for observing the left image by the left eye and the other for observing the right image by the right eye of an observer. Preferably, each optical path begins with an objective lens that is capable of seeing a broad image area and directing the image to a pair of angled mirrors or prisms. The mirrors or prisms in turn send the image through an eyepiece into one eye of the observer. The separation between the two eyepieces is adjustable to suit different observers. The separation between the two objective lenses is designed to be in accord with the dimensions of and the separation between the two images to ensure a broad viewing field. This pair of optical paths preferably are provided with a vertical movement means which is in turn supported by a sturdy stand. This vertical movement provision permits the observer to cover a wider viewing area in case that the display screen is wider than the range covered by the pair of objective lenses when in one specific height.

In yet another embodiment, the two video display devices are replaced by two film-holding means, which are comprised of flat glass plates back-illuminated with fluorescent lamps and clipping means to hold radiographic films in place.

In summary, the present invention discloses improved apparatus for stereoscopically displaying radiographic images of the internal structure of an object and for determining the spatial coordinates of selected feature images inside the object. The apparatus makes it possible to conduct a new stereo radiography method that is composed of the following steps: (a) producing a pair of images on the same object at slightly different angles with image reference markers being placed on specified positions of the top or bottom surface of the object when irradiated; (b) using image display devices to present this pair of images; the two images are to be set up in a definitive orientation so that when the images are viewed by the two eyes of an observer, the two lines of sight that connect the two eye balls with the corresponding image points of the image pair intersect; the two images being respectively provided with two stationary, transversely aligned reference lines across the image plane in the Y-direction; (c) using two distinct optical paths to permit viewing of the left image by the left eye and the right image by the right eye independently, as well as viewing of the images with both eyes simultaneously; (d) performing and measuring horizontal shifting motions of the two images according to a sequence of steps to be specified at a later section. These steps basically involve aiming and aligning the image points of a reference marker with their respective reference lines. Preferably, the same procedures are followed again for a second marker. The same procedures are then repeated to align the image points of a selected internal feature (e.g., a defect) with their respective reference lines. These procedures are carried out to allow for more convenient and accurate measurements of various image parallax values, which are in turn used to precisely calculate the location of an internal feature image of interest. The above steps are further illustrated in more detail in what follows:

DETAILED DESCRIPTION OF THE PREFERRED EMBODIMENTS

As required, detailed embodiments of the present invention are disclosed herein. The described embodiments are to be understood as merely exemplary of the invention, which may be embodied in various forms. Therefore, specific structural and functional details disclosed herein are not to be construed as limiting, but merely as a basis for the claims and as a representative basis for teaching those who are skilled in the art to variously employ the present invention for a wide range of appropriately detailed structures.

Figure 1A:
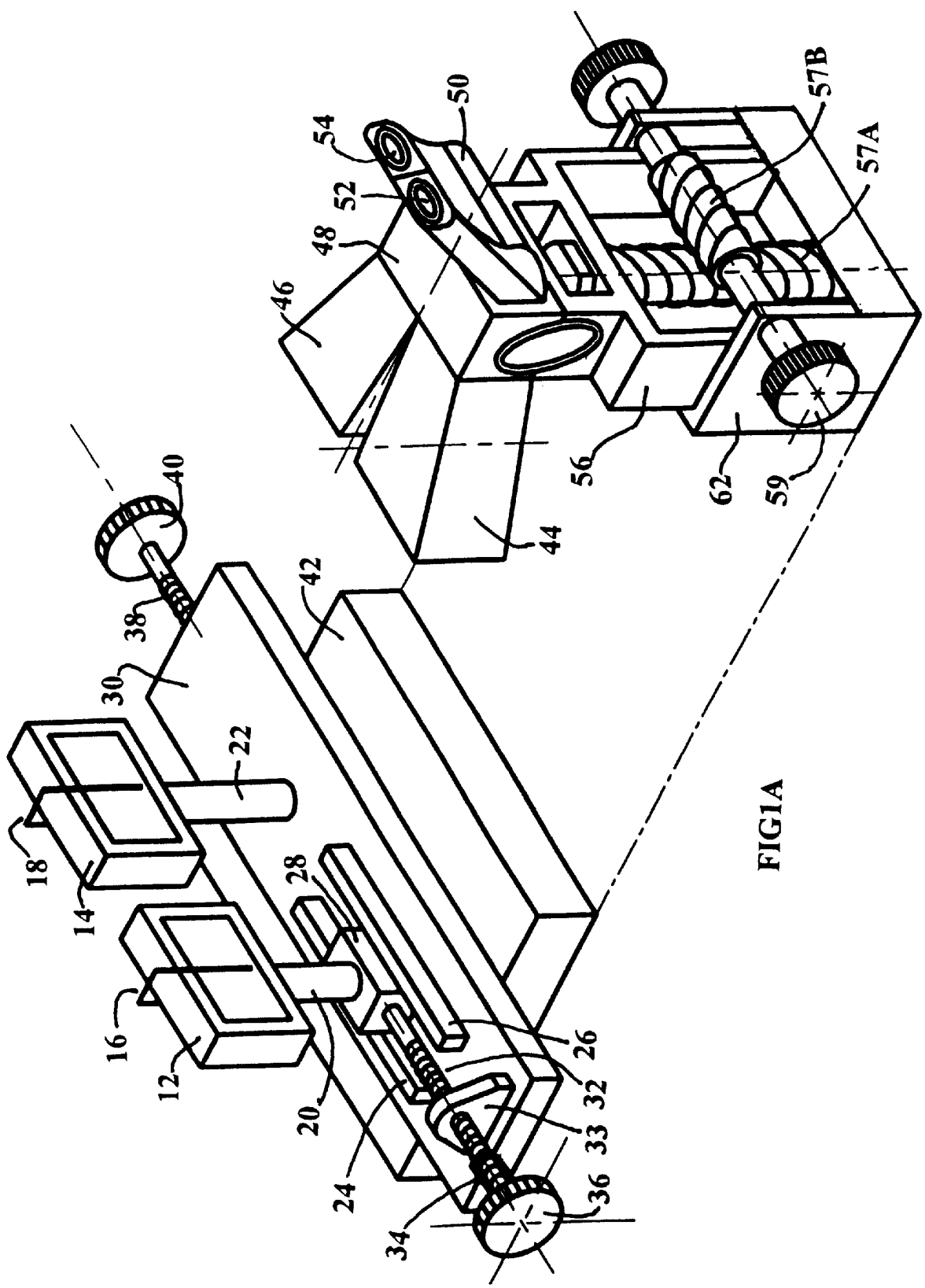
FIG. 1(A) Schematic showing t he major components of a preferred design for a stereoscopic radio graphic image observing and measuring apparatus (the image-displaying portion and the optical observing portion are separated to permit better viewing). (B) Same apparatus as in (A), but with the two portions brought closer together. (C) Similar apparatus as in (A), but the reference lines are attached to the proximal ends of the optical paths.
Figure 1B:
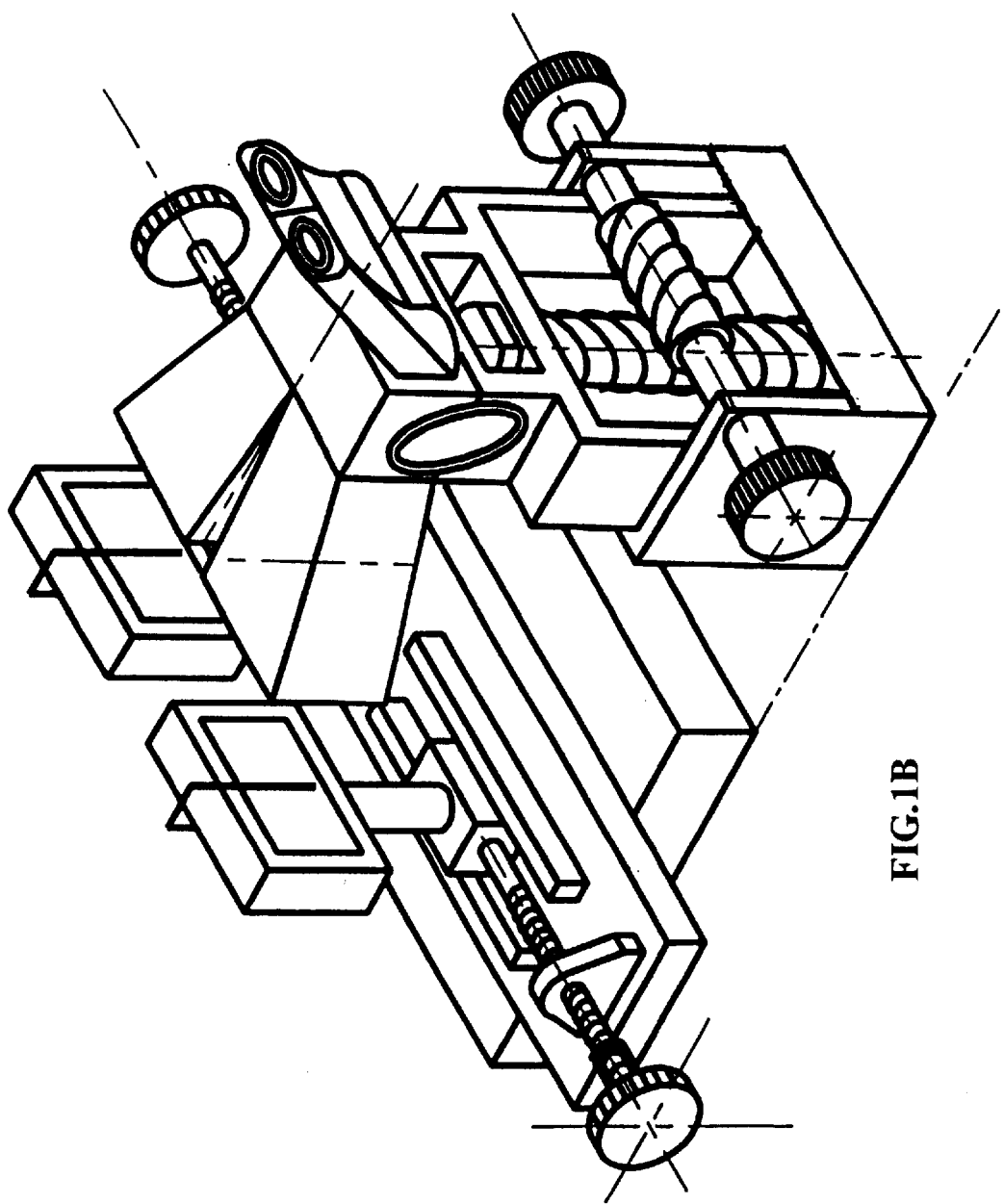
Figure 1C:
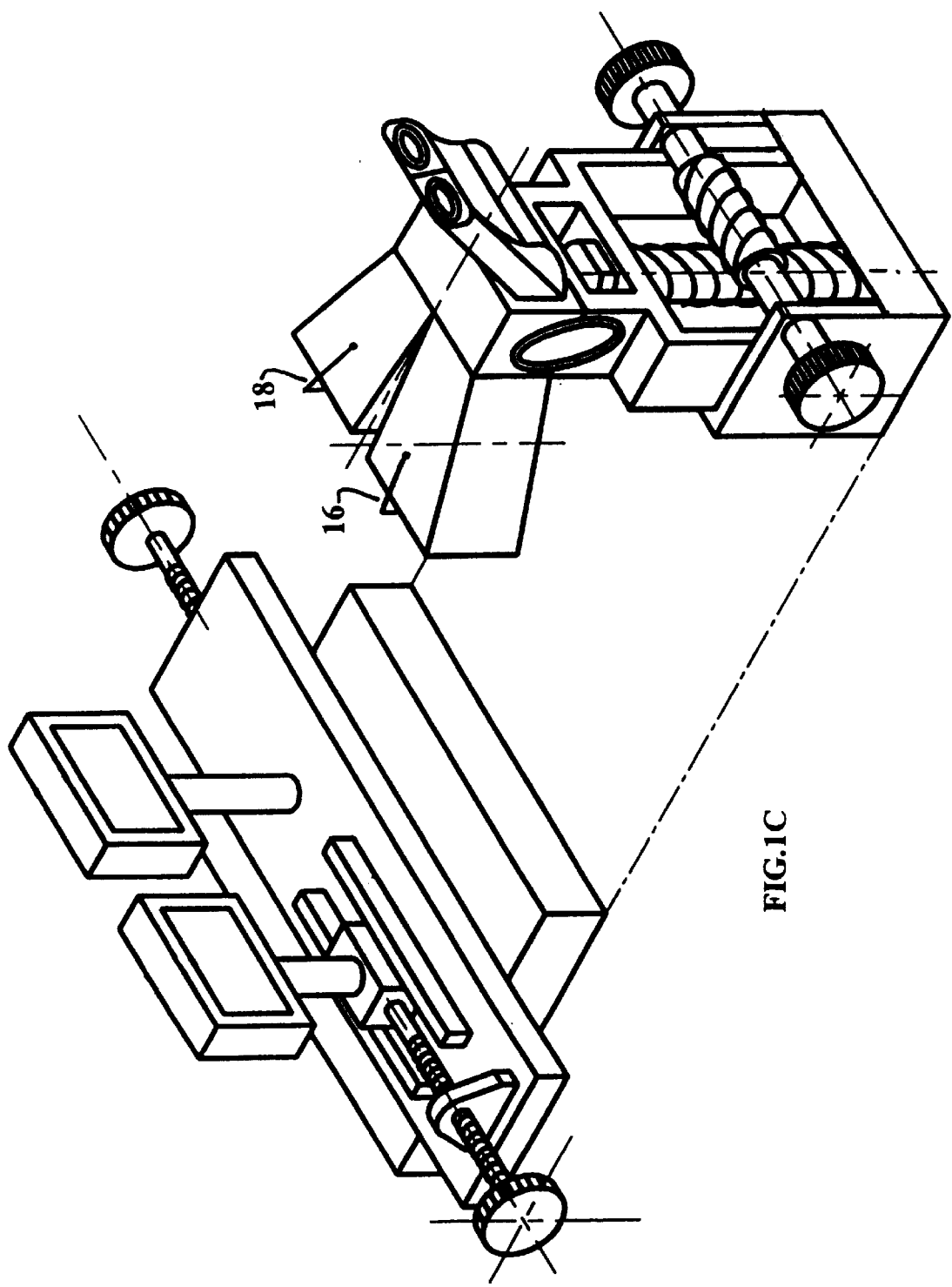

Referring to the drawings in more detail, FIG. 1A and 1B schematically show the major components of a preferred design for a quantitative stereoscopic radiograph analyzing apparatus. Two video display devices 12, 14 are used to display a pair of radiographic images. Two reference lines 16, 18 are provided across the respective screens of the two display devices. These two reference lines may be two thin opaque wires located in front of, but very close to, the screen plane. These wires may be physically held in place by fastening means (not shown) on the apparatus base 42. These wires are not allowed to move along with the display devices 12,14 and will provide the necessary position references for measuring the image shifts and defect locations (to be explained later). A further preferred embodiment is shown in FIG. 1C, in which the two reference lines are attached to the casings 44,46 of the optical paths. This arrangement ensures that the two reference lines remain stationary and within the viewing field of the operator's eyes even when the video display devices are shifted. Each reference line can be just a laser-etched line on a transparent glass plate attached to the proximal end (close to the corresponding image display device) of the optical path.

Both image display devices are supported by a slidable platform 30, referred to as the primary platform, through their respective stands, 20 and 22. One of the two video display devices (shown to be the left one 12 in FIG. 1A, but could have been the right one 14), through its stand 20, is positioned on a slidable platform 28, referred to as the secondary platform. The stand 20 is fastened to or, preferably, integrated with platform 28. Also, the stand 22 is fastened to or, preferably, integrated with platform 30. Platform 28 is allowed to slide horizontally in the "X" direction between two guiding posts 24, 26 forming a trough to slidably accommodate platform 28. The sliding movement of platform 28 may be driven by any drive means. Shown in FIG. 1A is a simple driving mechanism that is constituted by a threaded shaft 32, supported by a shaft housing 33, a micrometer 34, and a turning handle 36. By turning the handle 36, one can advance or retreat the shaft screw 32 to drive the secondary platform 28 horizontally. The motion of the shaft may be either manually driven (e.g., by spinning the handle to a desired number of turns) or driven by any power tool (e.g., an electrical motor, hydraulic piston, pneumatic, solenoid, or other types of actuators). What is schematically shown in the left portion of FIG. 1A represents one of the many common sliding mechanisms that can be utilized to generate reversible sliding motions for a part. Those who are skilled in mechanical art may select from a wide array of sliding mechanisms that are commonly used and are mostly commercially available. For example, those worm shaft-worm gear combinations commonly used in moving the platforms of a milling machine or a lathe may be used for moving the secondary platform and measuring its travel distance. A large number of linear motion slides or actuators for the purpose of positioning are commercially available. Similarly, a drive means, represented by 38,40 is also provided for the primary platform 30, to move the two images simultaneously in the "X" direction. A displacement measuring means, such as a micrometer, is provided for this primary platform. The secondary platform 28 is used to horizontally shift one image with respect to the other. The two drive mechanisms need not be of same type or dimensions. The complete assembly is supported by a sturdy base 42.

The micrometers are connected in-line to measure the sliding distances of both platforms. Again, there are many simple ways of measuring the travel distance of a part. One may choose to use an optical encoder, laser beam, or just a simple sliding caliper, etc. To use any other type of drive means or travel measuring means in the present context would merely represent a simple variation of the present invention. In a further preferred embodiment, the micrometer may be replaced by or supplemented with a displacement sensor that is capable of converting the mechanical displacement data into electrical signals in analog form. These sensors are very commonly used in the field of physical measurements. Examples include the linear variable differential transformer (LVDT) or an extensometer-type sensor commonly used in the mechanical testing of materials. Preferably, the analog signals are further converted into digital signals through an analog-to-digital (AD) converter means. These digital signals then are directly displayed in a digital display means such as a liquid crystal display. These signals may also be further used by a computer to calculate the acquired image shift distances and the spacial coordinates (X,Y,Z) of an internal feature of an object.

Figure 2:
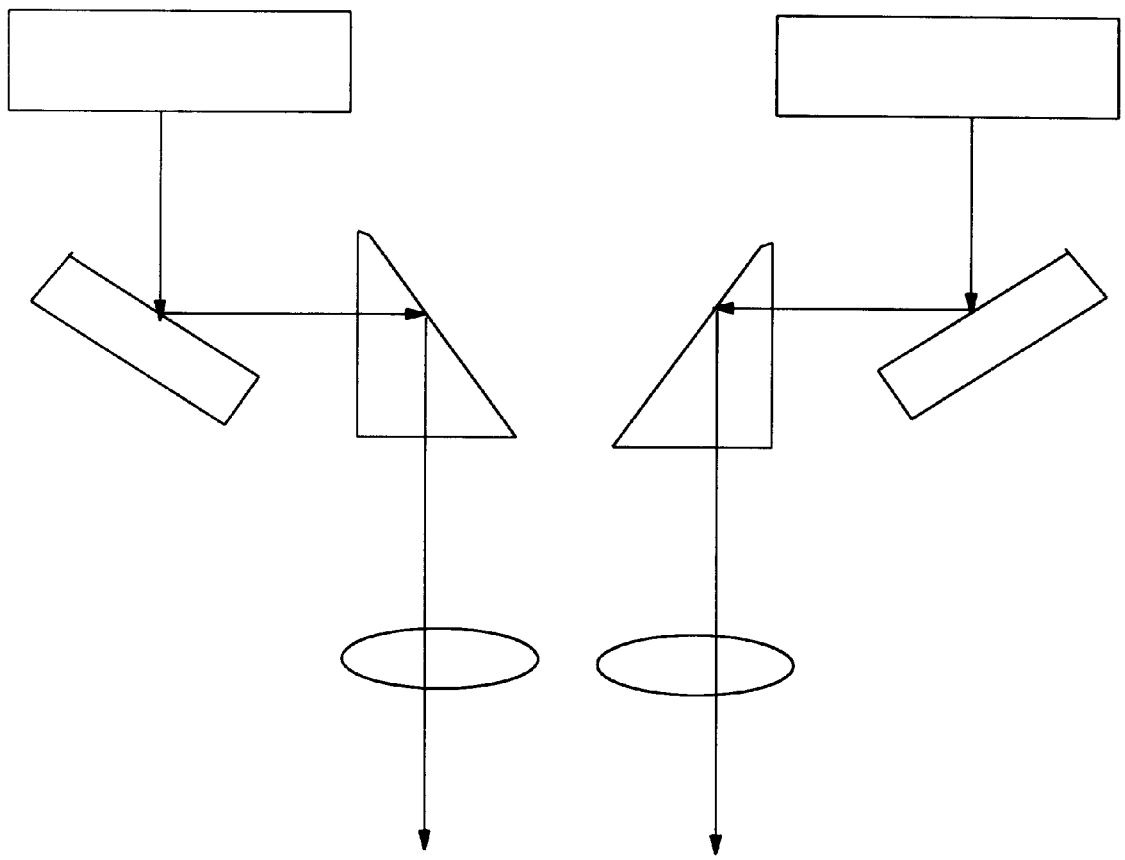
FIG. 2 Schematic showing the two optical paths in the observing compartment.

The two images shown on the screens of display devices 12,14 are to be viewed by the observing unit of the present invention, shown on the right lower portion of FIG. 1A. Housed in casings 44,46,48 are mirrors and lenses that are required to direct the light from the two images to an adjustable binocular 50 including two eyepieces 52,54. This optical assembly, 44 through 54, provides two distinct and separate optical paths to meet the parallax requirement of generating a stereo perception; i.e. an image recorded from the perspective of the right eye now can be seen by the right eye while an image recorded from the perspective of the left eye can be seen by the left eye. The arrangement of the two optical paths is schematically shown in FIG. 2, in which the two images 70,72 are respectively reflected and re-directed through two reflector means (mirrors or prisms 74,78 and 76,80), and then through the lenses 82,84 in eyepieces 52,54 into the left and right eye of an observer.

The optical path assembly is supported by a stand 56, which preferably has a height-adjusting means (e.g., a warm gear-shaft combination 57A, 57B) to move the assembly up and down as desired. Any releasable fastening means with sliding provisions, any linear motion device, any proper ball bearing-screw combination or chain-wheel combination possibly driven by a motor means (or manually driven by rotating a hand wheel 59), can be set up to drive the optical assembly up and down. The stand 56 is supported by and accommodated in a second sturdy base 62, which can be connected to or integrated with the first sturdy base 42 of the two platforms.

The operating principles for the presently invented quantitative stereoscopic radiography apparatus may be best illustrated by referring to FIGS. 3–7. Prior to taking radiographs or generating X-ray images on an image intensifier, the image orientation must be defined and reference markers established. Reference markers are set up to meet the need to establish a reference coordinate system. For example, in order to measure the vertical depth from the top surface of an object to an internal flaw, a small-sized lead marker may be placed on the top surface of the object. The basic procedures for carrying out radiography are shown in FIG. 3A. An imaging plate P (a radiographic film, an image intensifier device, or any other image recording plate) is placed behind the object. An image is produced on plate $P_1$ at a focal length F with the radiation source located at $S_1$. On this image plate $P_1$ are shown the image point $g_1$ of a reference marker G and the image point $a_1$ of a flaw A. The radiation source is then shifted laterally in the "X" direction by a distance B to a new position $S_2$ while the object remains stationary. A second image is then produced on plate $P_2$ with a focal length F. This plate $P_2$ now contains the image point $g_2$ of G and the image point $a_2$ of A. Alternatively, one may choose to maintain the radiation source stationary while shifting the object laterally by a distance B (FIG. 3B). With all other parameters maintained constant, both modes of image acquisition will yield the same results.

Figure 3A:
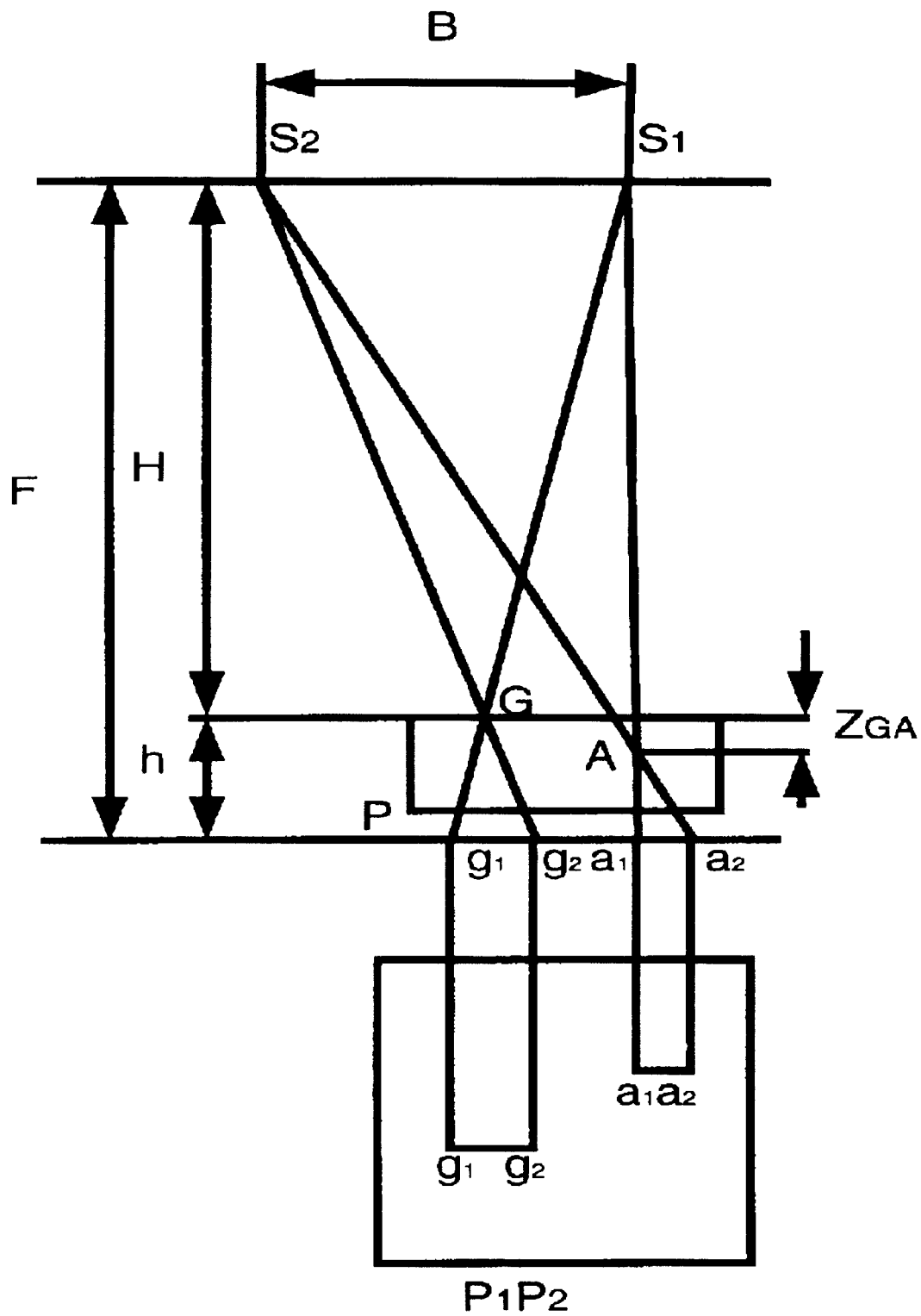
FIG. 3(A) Geometrical relationships between a lead marker G, an internal defect A, and their images $g_1$, $g_2$ and $a_1$, $a_2$ on a radiographic film or image intensifier screen (referred to as image plane, p). An image is recorded (e.g., a radiograph $P_1$ is taken) when the X-ray source is located at $S_1$. A second image is recorded (e.g., a second radiograph $P_2$ is taken) when the source is at $S_2$. (B) The corresponding situation where the two images are taken sequentially; the second image is taken after the object is shifted laterally while keeping the X-ray source stationary.
Figure 3B:
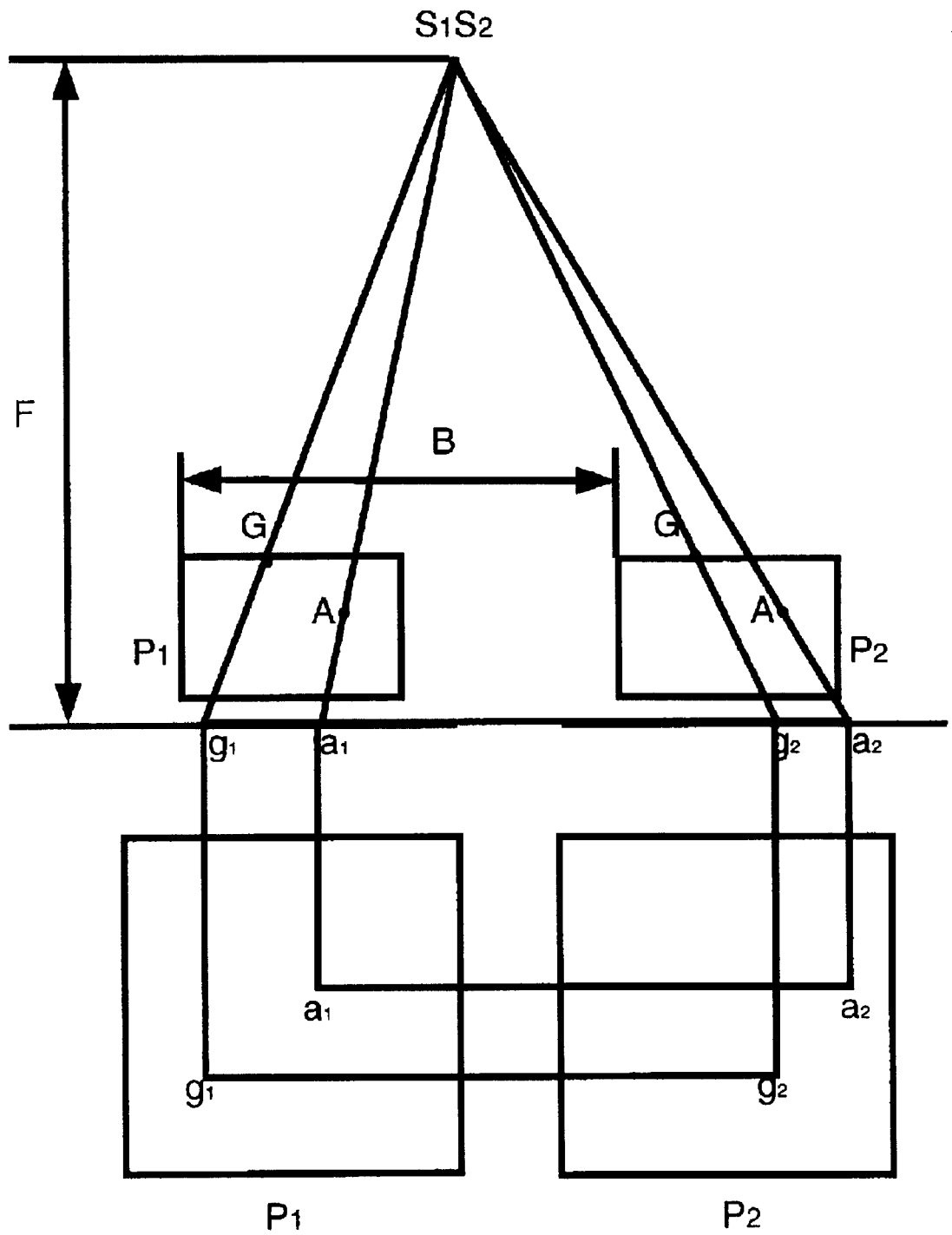
Figure 4:
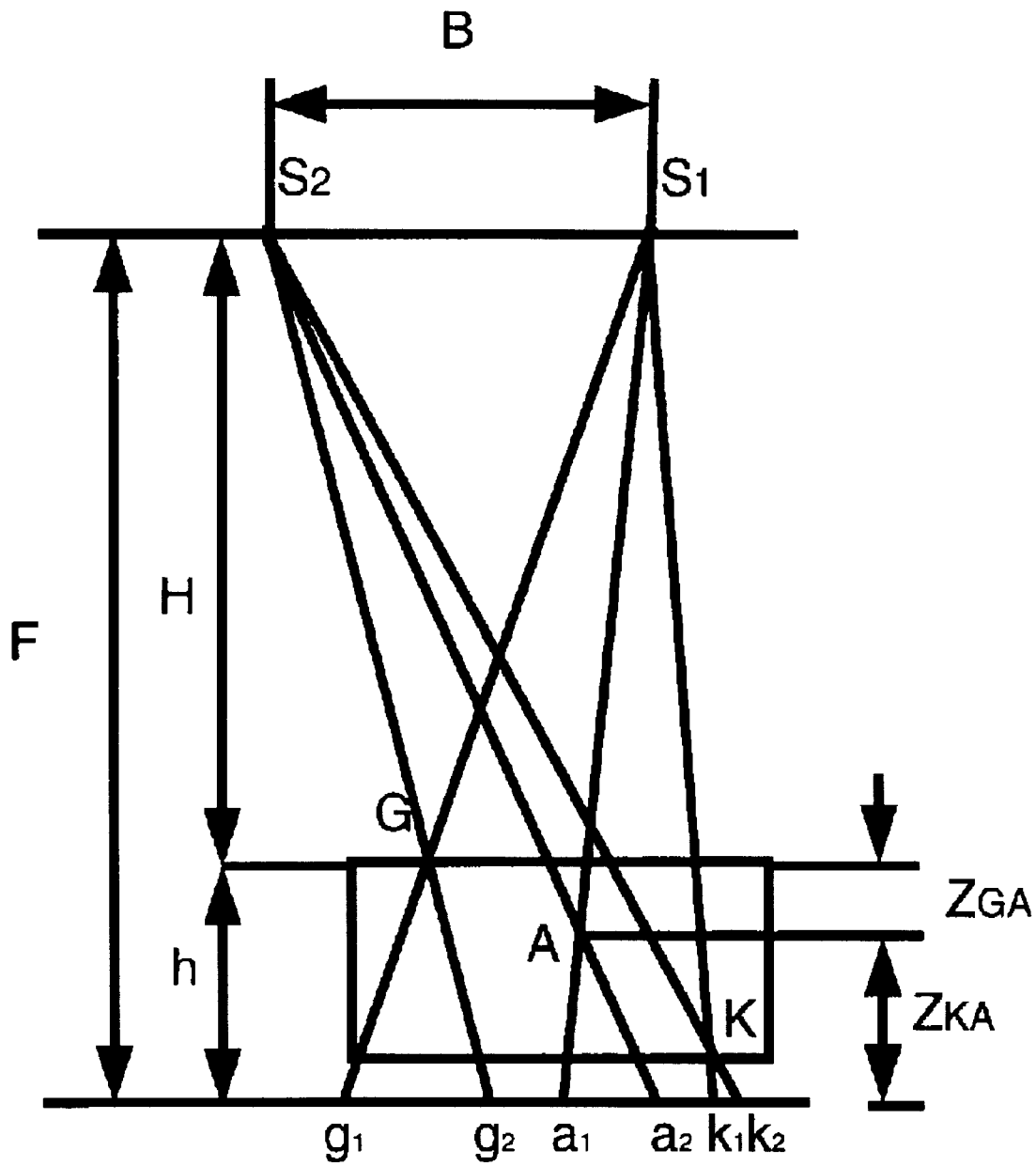
FIG. 4 Geometrical relationships between two lead markers G, K, an internal defect A, and their respective images $g_1$, $g_2$, $k_1$, $k_2$ and $a_1$, $a_2$ on a radiographic film or an image intensifier screen. This diagram helps illustrate the derivation of the formulae used in depth calculations of internal defects.

Referring to FIG. 3A, the depth from the reference marker G to flaw point A may be derived as follows: Let $Z_{GA}$ be the vertical distance from point G to point A, h the distance from the top surface of the object to the imaging plate, then H=F-h. (Related mathematical symbols are herein defined:~means "being similar between two triangles"; ∵ means "because"; ∴ means "therefore"; Δ, when followed by three letters, denotes a triangle; $a_1,a_2$ means the distance between $a_1$ and $a_2$).

$$\because \Delta S_1 A S_2 \sim \Delta a_1 A a_2 \qquad (a)$$

$$\therefore \frac{a_1 a_2}{B} = \frac{h - Z_{GA}}{H + Z_{GA}} \quad \text{Then } Z_{GA} = \frac{B \cdot h - a_1 a_2 \cdot h}{B + a_1 a_2}$$

$$\because \Delta S_1 G S_2 \sim \Delta g_1 G g_2 \qquad (b)$$

$$\therefore \frac{g_1 g_2}{B} = \frac{h}{H} \quad \text{Then } h = \frac{g_1 g_2 \cdot H}{B}$$

Substitution of (b) into (a) gives $$Z_{GA} = \frac{(g_1 g_2 - a_1 a_2) H}{B + a_1 a_2} = \frac{H}{B}(g_1 g_2 - a_1 a_2) \cdot \left(1 + \frac{a_1 a_2}{B}\right)^{-1} \qquad (c)$$

In a normal radiographic image taking situation, $Z_{GA} \ll H$, hence $a_1 a_2 \ll B$; therefore, Eq.(c) may be simplified as:

$$Z_{GA} = \frac{H}{B}(g_1 g_2 - a_1 a_2) \qquad (d)$$

In Eq.(d), H and B can be determined during the image taking step, $(g_1 g_2 - a_1 a_2)$ can be measured by examining the images on plates $P_1$ and $P_2$. Therefore, $Z_{GA}$ can be readily calculated provided that the apparatus permits determination of $(g_1 g_2 - a_1 a_2)$. The detailed procedure for determining $(g_1 g_2 - a_1 a_2)$ is given as follows (see FIG. 7):

Step 1: Place the images of plates $P_1$ and $P_2$ in a correct orientation according to the directional marks of the plate; e.g., Letters "L" and "R" may be labeled on the two radiographic films to help identify the left and right images, respectively.

Step 2: Gently shift the primary platform 30 while observing the image from $P_2$ by right eye only until the right image point $g_2$ falls on the right reference line 18.

Step 3: Gently move the secondary platform 28 while observing the image from $P_1$ by left eye only until the left image point $g_1$ falls on the left reference line 16. Then observe by both eyes while moving the secondary platform slightly in the "X" direction to ensure that the reference line is at the same depth as the image $g_1$ (and $g_2$) of point G. At this moment, record the travel distance of the secondary platform (e.g., the reading on the micrometer 34 is read off as $P_G$).

Step 4: Move the primary platform to bring image $a_2$ to fall on the right reference line 18.

Step 5: Move the secondary platform to bring image $a_1$ to fall on left reference line 16 (using left eye only). Observe by both eyes and move the secondary platform slightly in the "X" direction, make sure the reference line is at the same depth as point A, and then record the travel distance of the secondary platform (the micrometer reading now shows $P_A$); Here, $P_G - P_A = \Delta P_{GA} = (g_1 g_2 - a_1 a_2)$. By substituting the value of $(g_1 g_2 - a_1 a_2)$ into Equation (d), one obtains $Z_{GA}$, the depth of defect A with respect to reference marker G.

In actual radiography practice, the focal length F may not be accurately measurable, resulting in some inaccuracy in defining H=F-h. Consequently, there may be a large error with $Z_{GA} = H/B \Delta P_{GA}$. In order to overcome this potential problem, one may set up another lead marker K at the bottom surface of the object. Based on FIG. 4, another depth equation for $Z_{GA}$ may be derived as follows: A simple manipulation of Eq.(b) leads to $H = Bh/g_1 g_2$ which, upon substitution into Eq.(d), gives $$Z_{GA} = \frac{h}{g_1 g_2}(g_1 g_2 - a_1 a_2) = h\left(1 - \frac{a_1 a_2}{g_1 g_2}\right)$$

$$\because a_1 a_2 = Ka_1 - Ka_2; \quad g_1 g_2 = Kg_1 - Kg_2;$$

$$\therefore Z_{GA} = h\left(1 - \frac{Ka_1 - Ka_2}{Kg_1 - Kg_2}\right)$$

Let: $Ka_1 - Ka_2 = \Delta P_{KA}; \quad Kg_1 - Kg_2 = \Delta P_{KG}$

Then: $Z_{GA} = h\left(1 - \frac{\Delta P_{KA}}{\Delta P_{KG}}\right)$

Here, h is a parameter (the separation between the top surface of the object and the imaging plate) that can be measured accurately. Further, $\Delta P_{KA}$ and $\Delta P_{KG}$ are parameters that can be measured by the presently proposed apparatus. Their measurement procedures are the same as that for $\Delta P_{GA}$. Utilization of the above equations can significantly improve the accuracy for $Z_{GA}$.

Figure 5:
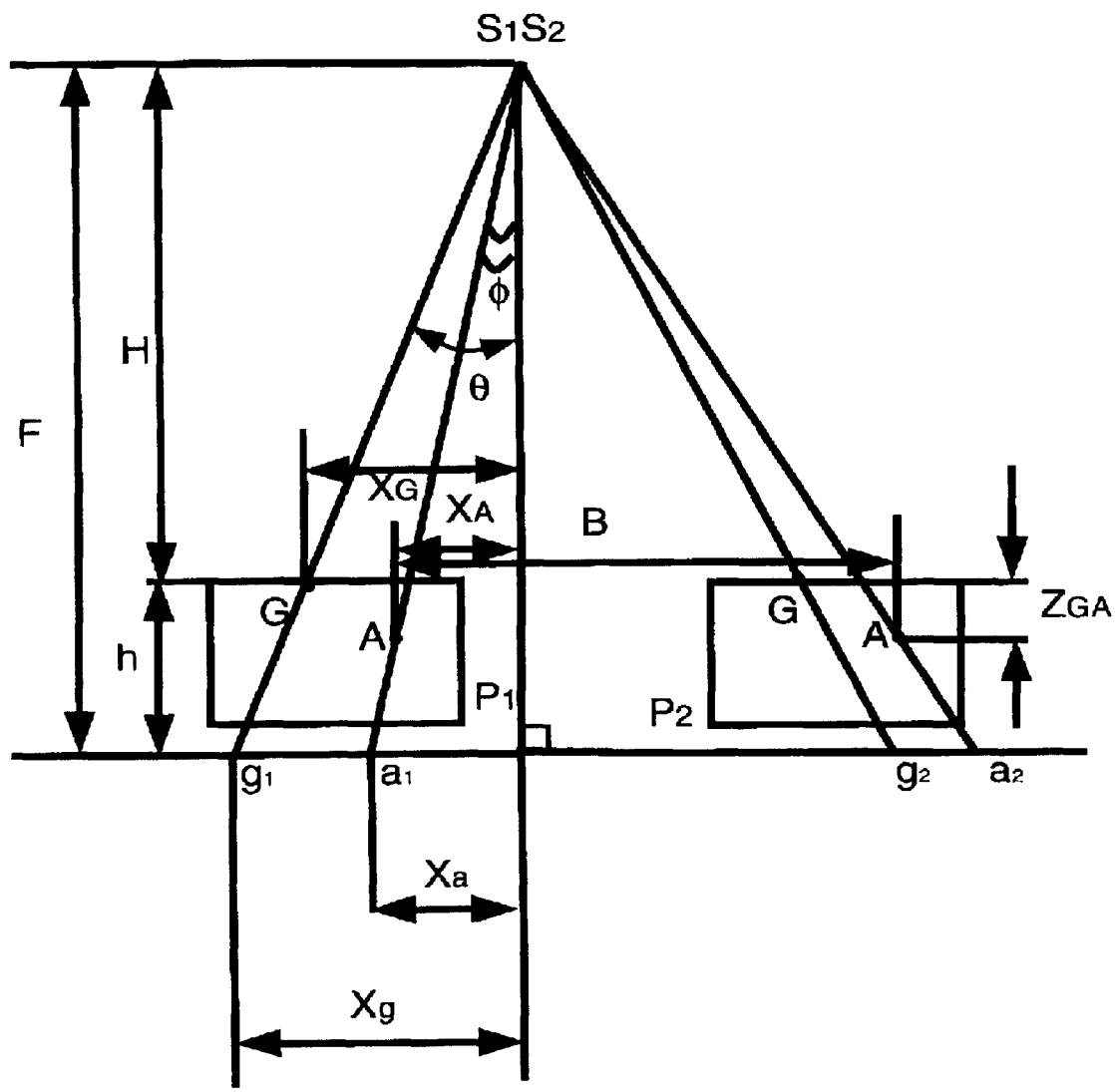
FIG. 5 Geometrical relationships between the lead marker G, an internal defect A, and their respective images $g_1$, $g_2$, and $a_1$, a2 on a radiographic film or an image intensifier screen. This diagram helps illustrate the derivation of the formulae used in the calculations of horizontal image shifts or the X-coordinate value of an internal defect position.
Figure 6:
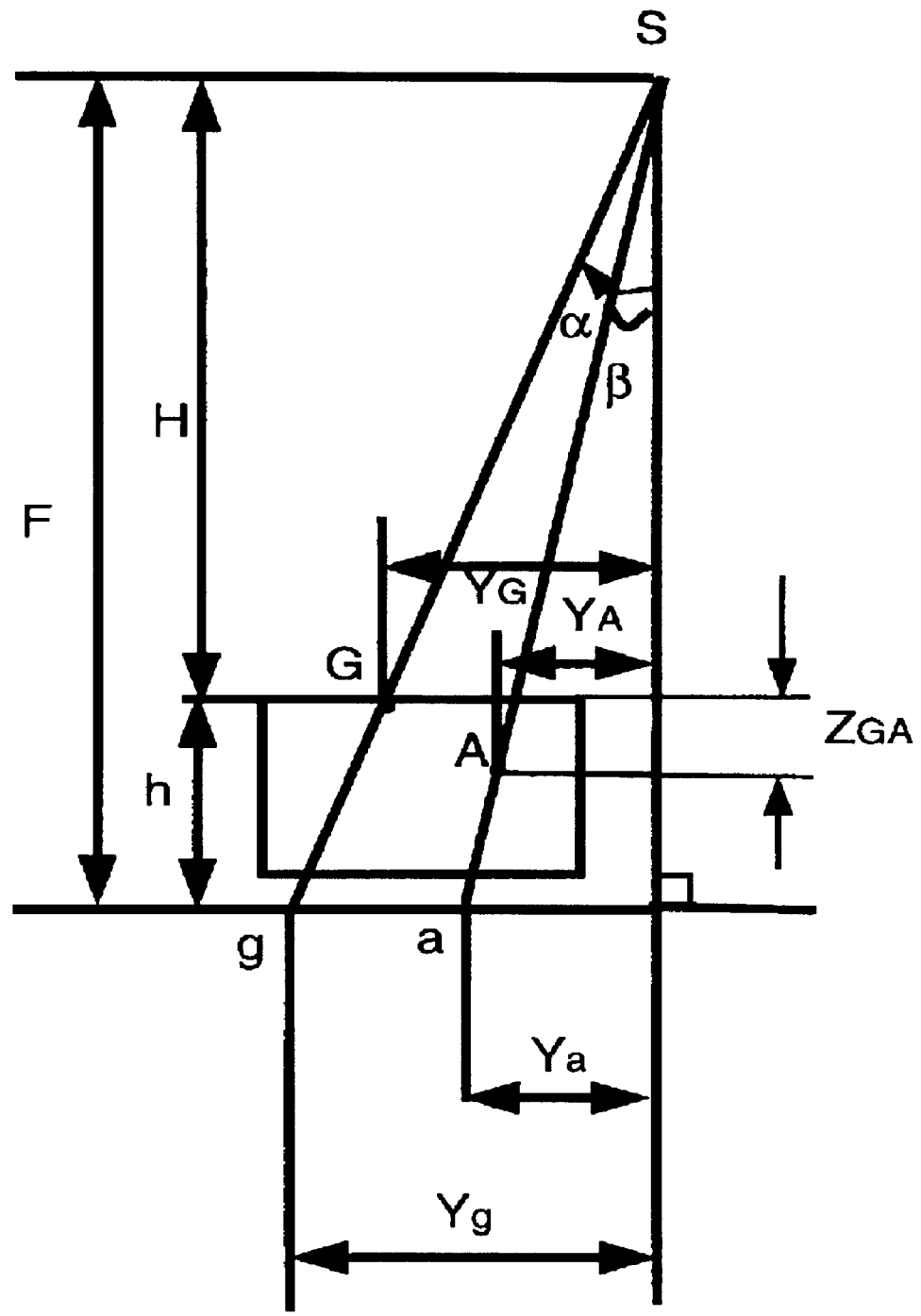
FIG. 6 Geometrical relationships between the lead marker G, an internal defect A, and their images $g_9$, $g_2$, and $a_1$, $a_2$ on a radiographic film or an image intensifier screen. This diagram helps illustrate the derivation of the formulae used in the calculations of transverse image shifts or the Y-coordinate value of an internal defect position.
Figure 7:
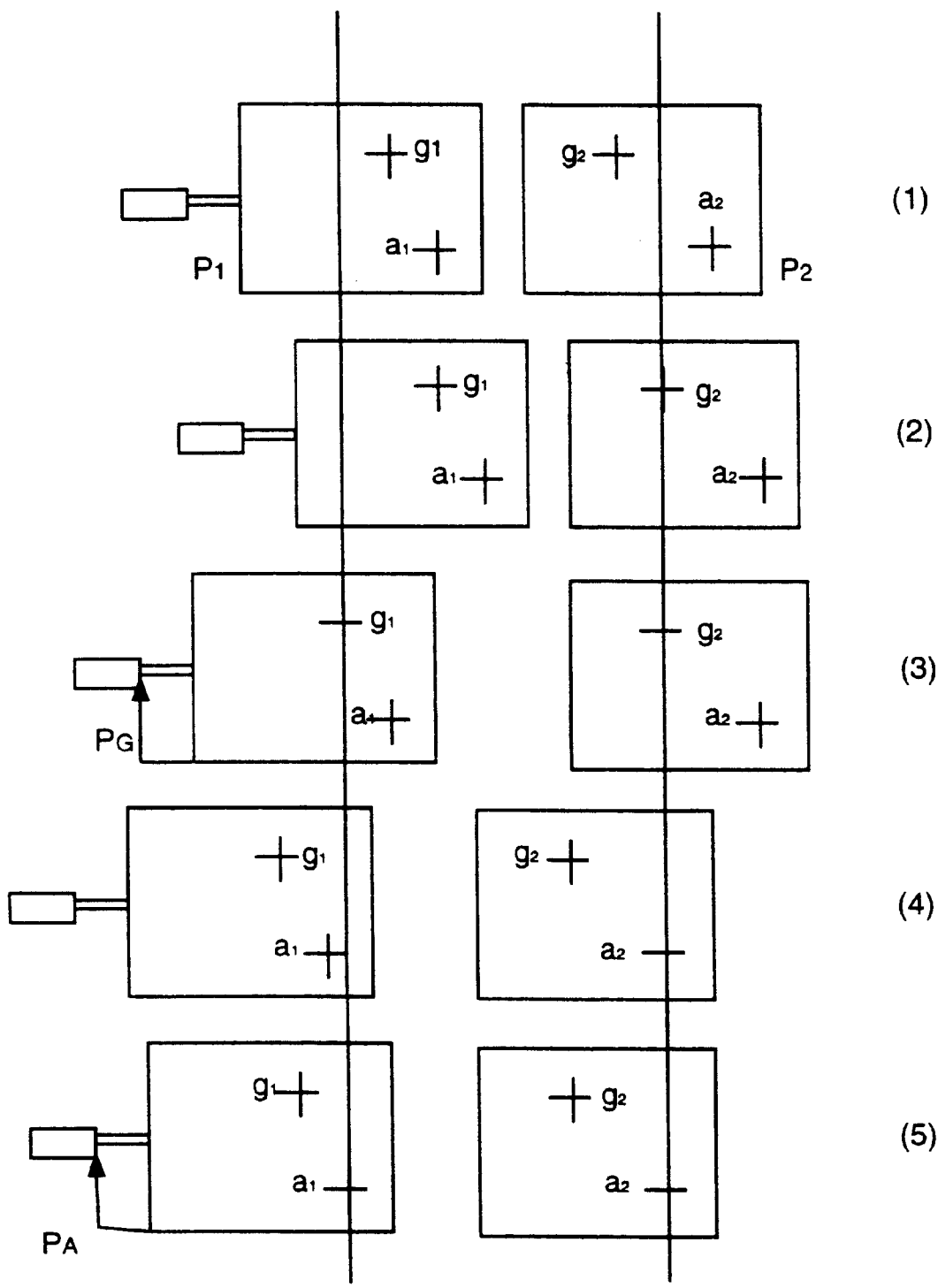
FIG. 7 Schematic showing the procedure to follow for measuring and calculating the depth of a defect.

Based on FIG. 5, the horizontal or "X" coordinate from flaw point A to reference marker point G can be derived as follows: Assume that the radiation source $S_1$ (or $S_2$) remained stationary while the object (and image plate P) was shifted for taking the second image. Draw a vertical line from he radiation source $S_1, S_2$ to the plate P. Let $X_{GA}$=the horizontal distance from point G to point A; $X_A$=the distance from point A to the vertical line; $X_G$=the distance from point G to the vertical line; $X_a$=the distance from point $a_1$ to the vertical line; $X_g$=the distance from point $g_1$ to the vertical line. Then, $$\because \tan\vartheta = \frac{X_G}{H} = \frac{X_g}{F}$$

$$\therefore X_G = \frac{X_g \cdot H}{F}; \quad X_g = \frac{X_G \cdot F}{H}$$

$$\because \tan\phi = \frac{X_A}{H + Z_{GA}} = \frac{X_a}{F}$$

-continued $$\therefore X_A = \frac{X_a(H + Z_{GA})}{F} ; X_a = \frac{F \cdot X_A}{H + Z_{GA}}$$

Also, let $\Delta Xag$ be the horizontal distance from the image point $g_1$ to image point $a_1$, then $\Delta Xag = Xg - Xa$. Substitution of the expressions for Xa and Xg into this equation leads to:

$$\Delta X_{ga} = \frac{F \cdot X_G}{H} - \frac{F \cdot X_A}{H + Z_{GA}}$$

$$\therefore X_A = \frac{(H + Z_{GA})(F \cdot X_G - H \cdot \Delta X_{ga})}{F \cdot H}$$

Since $X_{GA} = X_G - X_A$ and if the condition of $X_G = B/2$ can be met during the radiography imaging step, then $X_{GA}$ can be expressed as:

$$X_{GA} = \frac{B}{2} - \frac{(H + Z_{GA})\left(\frac{F \cdot B}{2} - H \cdot \Delta X_{ga}\right)}{F \cdot H}$$

where $\Delta X_{ga}$ is an unknown variable; however, it may be determined by examination of the image from $P_1$ with a transversely aligned ruler on the apparatus. Then, by plugging $\Delta X_{ga}$ into the equation for $X_{GA}$, one obtains the value of $X_{GA}$.

By following similar procedures, the longitudinal distance $Y_{GA}$ from the reference point G to flaw point A may be derived as follows (FIG. 6):

$$Y_A = \frac{F \cdot Y_G(H + Z_{GA}) - H(H + Z_{GA}) \cdot \Delta Y_{ga}}{H \cdot F}$$

Deducting from both sides of the equation by the same amount $Y_G$, one obtains $$Y_{GA} = \frac{\Delta Y_{ga}(H + Z_{GA})}{F} - \frac{Y_G \cdot Z_{GA}}{H}$$

In real practice, $Z_{GA} \ll H$, therefore, $Y_{GA} = (\Delta Y_{ga}H/F) - (Y_G Z_{GA}/H)$.

With the present radiography apparatus, one can use a transversely aligned ruler to measure $\Delta Yga$ directly on the image plate $P_1$ or $P_2$ and, therefore, readily obtain the value of $Y_{GA}$.

In the equations for $X_{GA}$ and $Y_{GA}$, F and H may or may not be accurately measured. In order to avoid the potential error, one may obtain the values of F and H through further calculations. Referring to FIG. 4 again:

$$\because \Delta S_1 GS_2 \sim \Delta g_1 G g_2$$

$$\therefore \frac{H}{B} = \frac{h}{g_1 g_2}$$

$$\because g_1 g_2 = kg_1 - Kg_2 = \Delta P_{GK}$$

$$\therefore H = \frac{h}{\Delta P_{GK}} \cdot B; \quad F = H + h = h\left(1 + \frac{B}{\Delta P_{GK}}\right)$$

In the above equations, $\Delta P_{GK}$ can be accurately measured by the proposed apparatus, the measurement method being the same as that for $\Delta P_{GA}$ described earlier with A replaced by K.

When viewing an object with both eyes, one sees different sides of the object from two different directions. Therefore, if a proper pair of perspective drawings, photos or other type of images corresponding to these two sides of the object are separately provided in front of their respective observing eyes, then the images on the retinas will provide a perception identical to what would have been visioned with both eyes. A 3-D optical image in space is thus sensed. This stereoscopic vision, obtained from viewing the preserved images, may be termed reproduction of the stereoscopic effect. The pair of drawings, photos or images of other form producing such an effect may be termed a "photo-couple". This kind of observation with a stereoscopic effect is herein referred to as stereoscopic observation.

The above-described principle of stereoscopic observation suggests that the following conditions must be fulfilled in order to obtain reproduction of the stereoscopic effect with a photo-couple: (1) A pair of images must be taken on the same object at slightly different angles; (2) The observer must be able to use his eyes separately in viewing the images at the same time, i.e. to make each eye see only the corresponding image separately and simultaneously; (3) The photo-couple must be set up in a definitive orientation, i.e. when viewing with both eyes, the two lines of sight from the corresponding image points of the photo-couple must intersect. The presently invented apparatus are designed to fulfill these conditions.

A further scrutiny on the general formulas derived above for the coordinates of feature points (e.g., defect points) in space suggests that one has to measure the parallax differences of the corresponding point images. Hence, the following conditions must be further fulfilled in the design and construction of a quantitative stereoscopic radiography instrument: (4) There must be a device or a pair of devices to display a pair of images; (5) Two distinct sets of optical systems (preferably with some magnifying capability) are needed to facilitate the viewing by each eye of the respective image independently and simultaneously; (6) Adjustments must be allowed for displacing the image display devices in the X- and Y-directions and for moving the eyepieces so that point images in various parts of the image plate can be seen. (7) The two images must be allowed to shift horizontally together in congruence as well as with respect to each other and there must be some devices for displacement measurements; (8) Reference lines and markers must be supplied for stereoscopic surveying. The presently invented apparatus have fully met the above-cited requirements.

Figure 8:
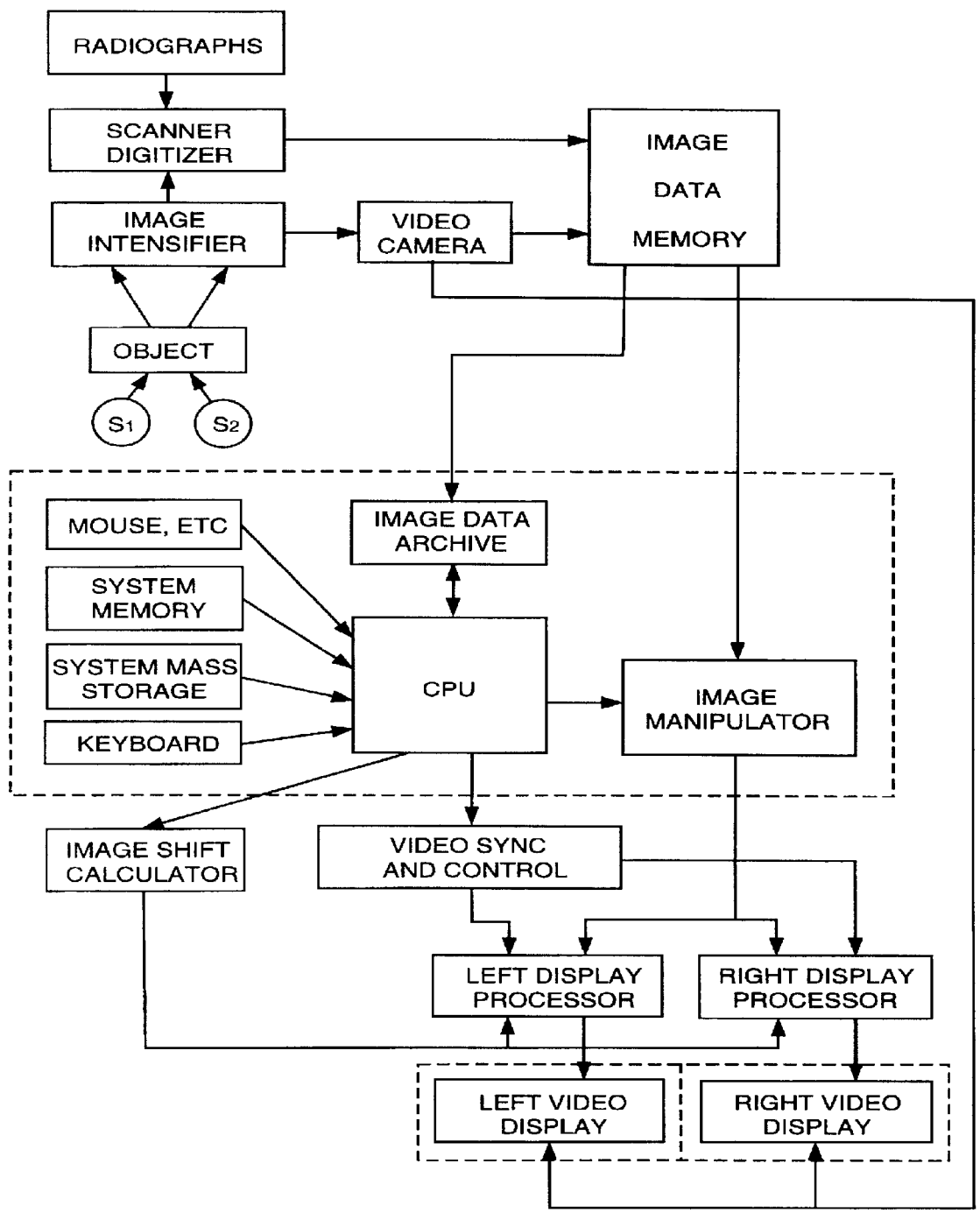
FIG. 8 A block diagram illustrating the major components and steps involved in the production and display of image pairs on video display devices.
Figure 10A:
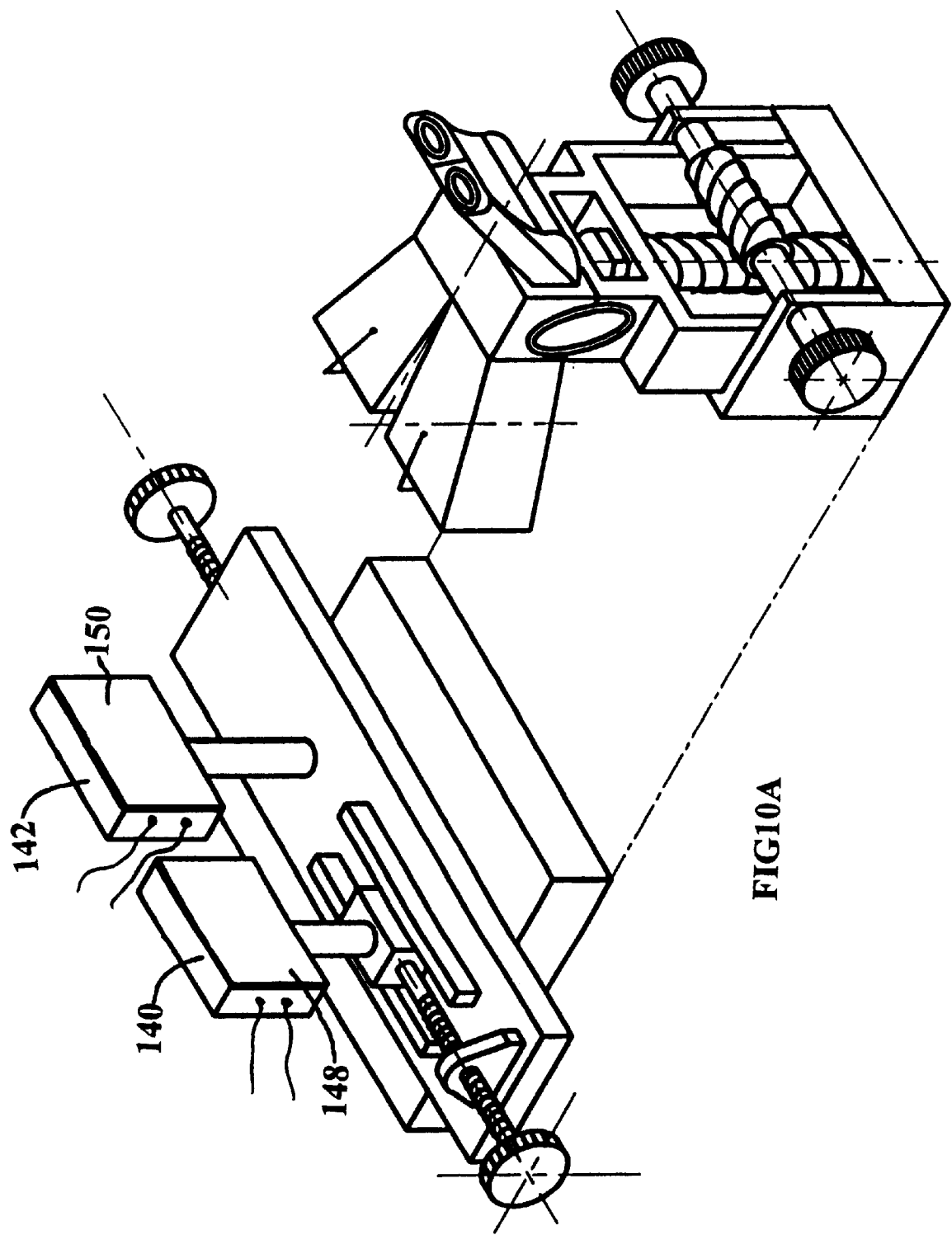
FIG. 10(A) Schematic drawing showing the major components of a design for a stereoscopic radiographic film observing and measuring apparatus (each film can be held vertically in place by clipping means on the front glass surface, back-illuminated by lamps). (B) a radiographic film-holding box with the front cover glass removed to reveal the illuminating lights.
Figure 10B:
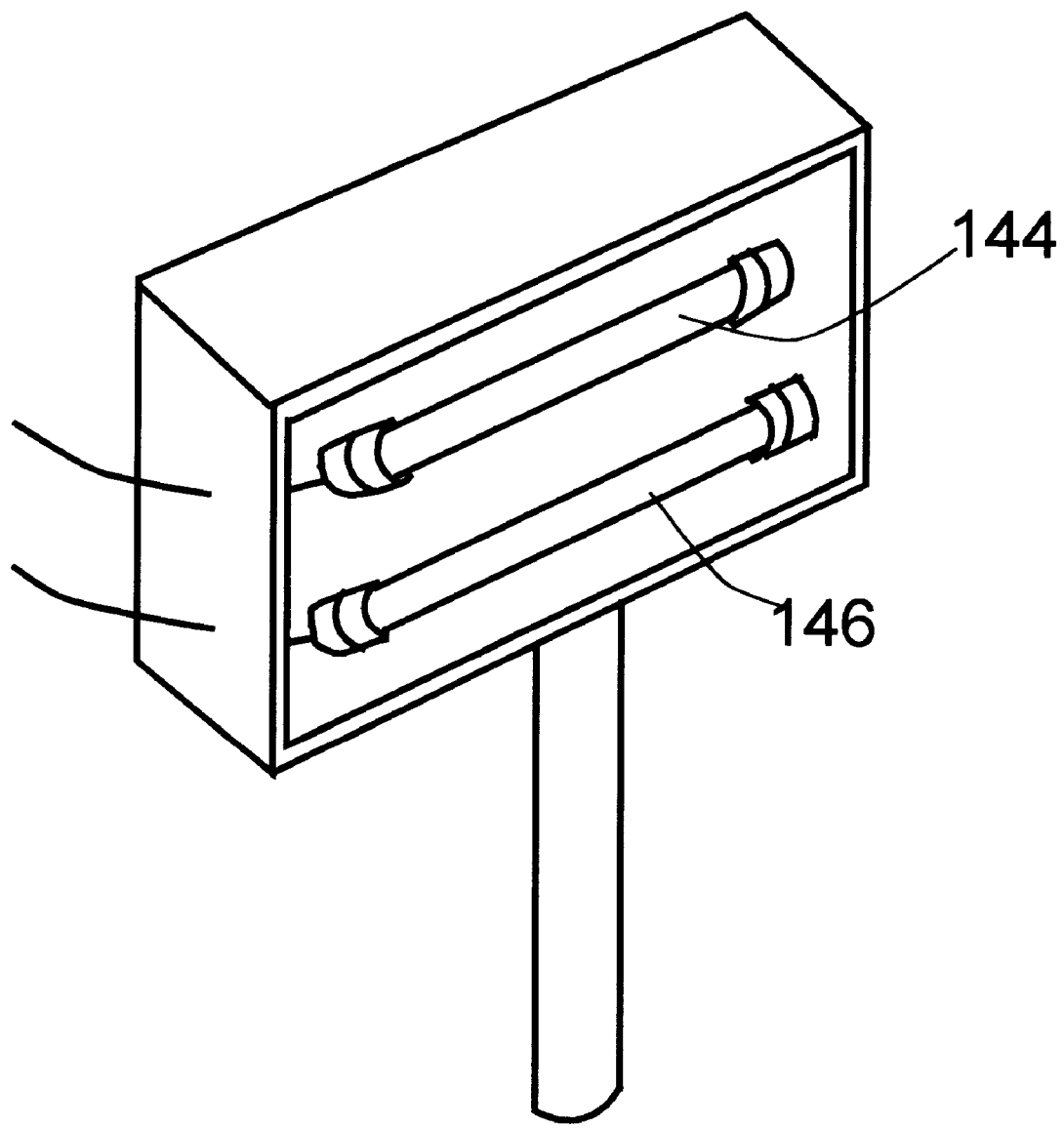

The nature of the image display devices is further specified herein. In its simplest form, the image plate may be just a radiographic film (negative film or transparency) or, less commonly, a positive print (opaque photographic paper). In the case of radiographic transparencies, a pair of film boxes 140,142 with back illuminating light 144,146 constitute the two required display devices (FIG. 10A and B). Clip means may be used to hold the radiographic films on the front glass surfaces 148,150 of the film boxes. When positive prints are employed, the two display devices are simply some devices that are capable of holding a pair of prints on their flat front surfaces. When deemed necessary, the front surfaces may be illuminated with proper lighting to facilitate observation. Alternatively, referring to FIG. 8, the images in radiographs (90, negative or positive) may be stored in an image data memory 94 through a commonly used scanner or digitizer 92 for further uses later.

In fluoroscopy radiography, the images picked up by an image intensifier 96 or flexible phosphor imaging plate may be recorded by a camera means 98, or other type of image reader/sensor, and stored in the image data memory 94. Commonly used image sensors include tube type TV cameras such as isocon, vidicons, and solid state charge coupled device (CCD) cameras. A linear diode array (LDA) can also be used to digitize and store the image to be viewed on a TV monitor. A flexible phosphor imaging plate is a two-dimensional sensor that can store a latent image obtained from X-rays, electron beams, or other types of radiation. This imaging plate is capable of sequentially reproducing the image as a digital file by releasing the photo stimulated luminescence (PSL) with a laser beam, piping the PSL to a photo multiplier tube (PMT) and then digitizing the resulting electrical signal. Generation of PSL light is accomplished via phosphor stimulation by a laser within what is called an "image plate reader". The reader also erases the plate making it available for reuse. Hence, one can generate one image, store this image in a memory device (or transfer it directly to the left image display device), erase this image from the plate, shift the X-ray source, generate a second image, and then store it in a memory device (or transfer it to the right image display device) to complete the production of a "photo-couple" for stereo spectroscopic analysis.

Memory 94 could be either an independent memory unit or a part of the mass storage 106 of a computer 99. The system computer 99 includes a central processing unit (CPU) 100, system memory 104, system mass storage devices 106, a keyboard 108, and a screen location selection device (e.g., a mouse 102). The mass storage devices 106 may include floppy disk drives and hard disk drives for storing an operating system. These storage devices 106 also store application programs for the system computer 99 and routines for manipulating the images shown on the image display devices 12,14 and for communicating with imaging devices such as a scanner or digitizer 92, image intensifier 96, or image data memory 94.

In one embodiment of the present invention, image manipulating routines are used to drive devices such as an image manipulator 114, image shift calculator 118, video synchronization and control 116, and video display processors 120,122. Many commercially available image processing packages contain the above image manipulating and calculating capabilities. This mix of devices 114,116,118, 120,122 are needed to provide capabilities of shifting the pair of images (photo-couple) horizontally together in congruency and with respect to each other, and computing the various image shift distances required in the calculation of the coordinates of an internal flaw.

Figure 9:
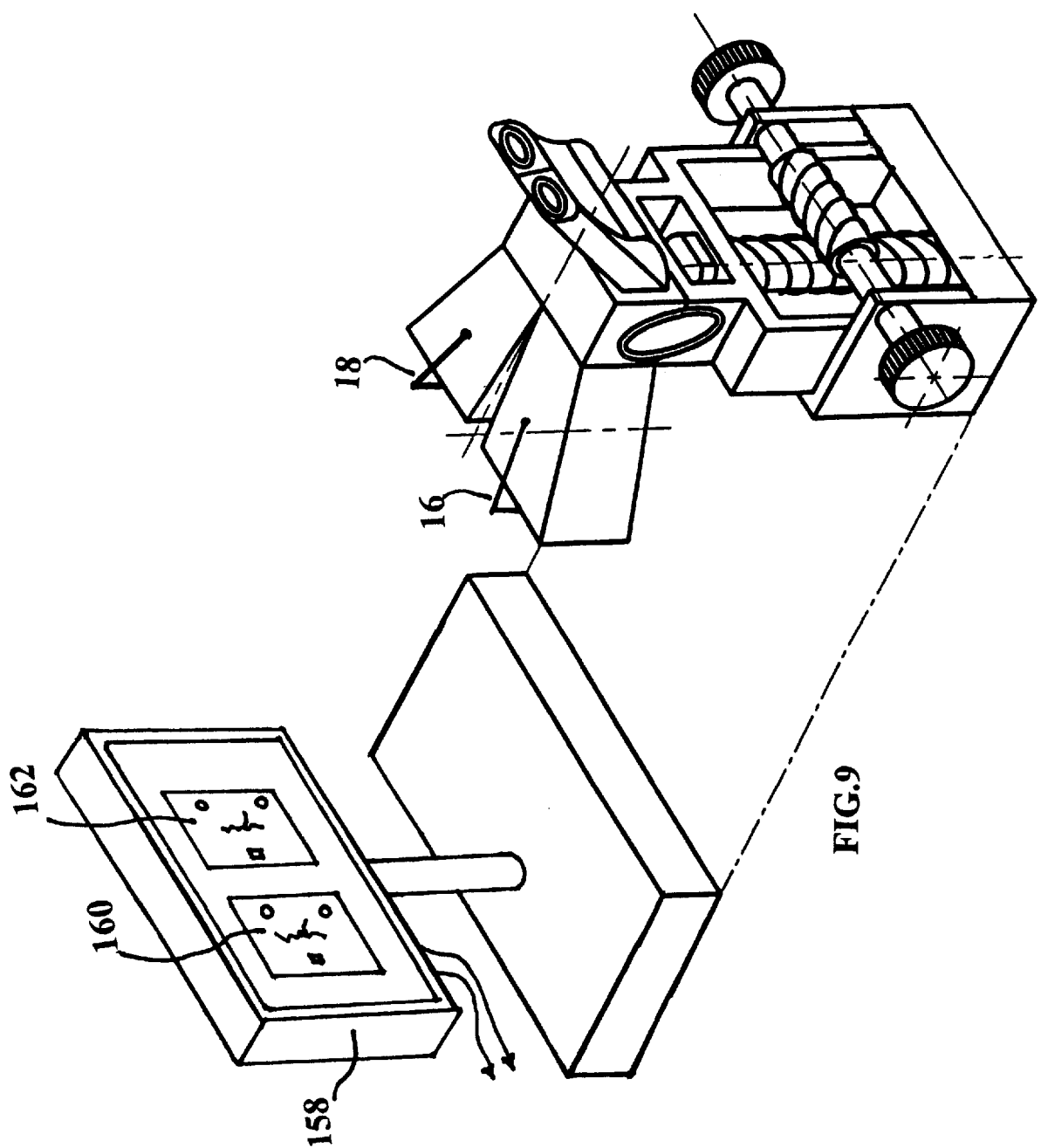
FIG. 9 Schematic drawing showing the major components of a design for a stereoscopic radiographic image observing and measuring apparatus (only one video display device is needed in which the two images can be shifted internally by executing a proper software program).

In another embodiment, the two images can be shown on the screen of an image display device (FIG. 9); only one image display device 158 is required. These two images 160,162 can be shifted together as well as shifted with respect to each other as desired. These shift distances can be measured through the execution of internal software programs of the above-cited image processing packages. In this case, the two reference wires 16,18 will be placed near the middle of the left portion and the middle of the right portion of the screen, respectively. The two references 16,18 can be just two internally generated lines or externally drawn straight lines that will remain stationary when the images are being shifted. Preferably, however, the two reference lines are thin wires that are attached to the proximal ends of the optical paths, as indicated in FIG. 9.

In yet another embodiment in which a minimal image manipulating capability is needed, the sole purpose of this capability is to deliver the images to their respective image display devices 12,14. Additional image enhancing functions to improve the image quality (resolution, contrast, etc.) are nice features to have, but are not strictly required. The movements of these images are to be executed by the primary platform 30 and secondary platform 28. In still another embodiment, at least one of the two image display devices has the capability of shifting the image horizontally with reference to the other image so that the secondary platform 28 can be eliminated. In this situation, the two image display devices 12,14 are both held in place by the primary platform 30, which provides simultaneous horizontal movements of the two display devices. The two display devices are maintained at a constant separation at all times.

It is to be understood that while certain forms of the present invention have been illustrated and described herein, the invention is not to be limited to the specific forms or arrangement of the parts described and shown.

What is claimed:

1. An apparatus for stereoscopically displaying a pair of left and right radiographic images that are taken from slightly different angles of an object and for determining the spatial coordinates of a selected feature image inside said object, comprising:

(a) two parallel image display devices, a left one for presenting said left image to the left eye and a right one for presenting said right image to the right eye of an observer; said two images being placed side-by-side along an X-axis direction of an X-Y-Z rectangular coordinate system, said X-axis being defined to be along a width direction of said images and lying approximately on a plane containing said images as well as being substantially parallel to the line segment connecting the two eyes of said observer; the Y-axis of said coordinate system being along the length direction of said images, perpendicular to the X-axis direction, and also lying approximately on said image plane with the Z-axis being normal to said image plane;

(b) a secondary platform to support said left image display device; said secondary platform being provided with movement means to reversibly displace said left image display device with respect to said right image display device horizontally in the X-direction; said movement means being equipped with displacement-measuring means to measure out an image shift distance;

(c) a primary platform to support said left secondary platform and said right image display device; said primary platform being provided with movement means to horizontally displace both image display devices congruently in the X-direction; said movement means being equipped with displacement-measuring means;

(d) a sturdy base in close proximity to support both secondary and primary platforms;

(e) an observing device in working proximity to said image display devices, comprising two parallel optical paths, a left one to direct said left image into the left eye of said observer and a right one to direct said right image into the right eye; each optical path comprising reflector means on one end proximal to said corresponding image display device and lens on another end with said lens encased in an eyepiece; said optical paths being housed and protected by a casing means which is connected to a supporting member; said supporting member being provided with drive means to move said optical paths transversely in the Y-direction; said supporting member being further supported by a sturdy base; and (f) two parallel reference lines transversely aligned in the Y-direction, a left reference line lying across a front end of said left optical path proximal to said left image and a right reference line lying across a front end of said right optical path proximal to said right image; said reference lines being held in place on said casing means by a fastening means.

2. An apparatus as set forth in claim 1 wherein said image display devices are video display monitors.

3. An apparatus as set forth in claim 1 wherein said image display devices are video display monitors which are electronically connected through image recording means to image intensifier means.

4. An apparatus as set forth in claim 1 wherein said image display devices are video display monitors which are in electronic communication with image storing and processing means; said image storing and processing means being in electronic communication through image recording means with image intensifier means.

5. An apparatus as set forth in claim 1 wherein said image display devices are video display monitors which are in electronic communication with the following image acquiring and processing devices:
  (a) image recording means to acquire images from a radiographic film, image intensifier, or flexible phosphor imaging plate;
  (b) a computer for image storing and processing, said computer being in electronic communication with said image recording means and comprising a system memory, system mass storage, a keyboard, a screen location-selecting device, and image manipulator and processor means.

6. An apparatus as set forth in claim 1 wherein each said image display device is a radiographic film supporting and illuminating means comprising a generally rectangular casing, an optically transparent plate attached to said rectangular casing to support a flat radiographic film, clip means to hold said film against a surface of said transparent plate, and a light source behind said transparent plate and inside said rectangular casing to illuminate said film.

7. An apparatus as set forth in claim 1 wherein said two parallel reference lines are two thin wires transversely aligned in the Y-direction, the left reference line lying across the front surface of said left image display device and the right reference line across the front surface of said right image display device; said reference lines being held in place by said sturdy base of the platforms so that said reference lines remain stationary while said primary or secondary platform is in motion.

8. An apparatus as set forth in claim 1 wherein said platform movement means are provided with
  (a) displacement sensor means to convert displacement data into a digital form;
  (b) electronic calculator means in electronic communication with said displacement sensor means to calculate image shift distances and the spatial location of a selected internal feature of said object; and
  (c) digital display means in electronic communication with said calculator means to show the calculated data values as desired.

9. An apparatus for stereoscopically displaying a pair of left and right radiographic images of the internal structure of an object and determining the spatial coordinates of a selected feature image inside said object, comprising:
  (a) two parallel video monitors; a left monitor for presenting said left image to the left eye and a right monitor for presenting said right image to the right eye of an observer;
  (b) image recording means in electronic communication with said video monitors;
  (c) a computer in electronic communication with said video monitors; said computer comprising a system memory, system mass storage, a keyboard, a screen location-selecting device, and image manipulator and processor means being capable of horizontally shifting said two images separately with respect to each other and simultaneously in congruency in an X-direction and calculating image shift distances; said X-direction being defined to lie approximately on a plane containing said images and approximately parallel to the line segment connecting the two eyes of said observer;
  (d) a sturdy base to support said video monitors;
  (e) an observing device in working proximity to said video monitors, comprising two parallel optical paths with a left path for directing said left image into the left eye of said observer and a right path for directing said right image into the right eye; each optical path comprising reflector means on one end proximal to said corresponding video monitor and lens on another end adjacent one of said observer's eyes with said lens encased in an eyepiece; said optical paths being housed and protected by a casing means which is connected to a supporting member; said supporting member being provided with drive means to move said optical paths vertically in a Y-direction, said Y-direction lying approximately parallel to said image plane and perpendicular to said X-direction; said supporting member being further supported by a sturdy base; and
  (f) two parallel reference lines transversely aligned in the Y-direction, the left reference line lying across a front end, proximal to said left image, of said left optical path and the right reference line lying across a front end, proximal to said right image, of said right optical path; said reference lines being held in place on said casing means by a fastening means.

10. An apparatus for stereoscopically displaying a pair of left and right radiographic images of the internal structure of an object and determining the spatial coordinates of a selected feature image inside said object, comprising:
  (a) one video monitor to present said two images side-by-side on the same monitor screen with said left image being observable by the left eye and said right image observable by the right eye of an observer;
  (b) image recording means in electronic communication with said video monitor;
  (c) a computer in electronic communication with said video monitor; said computer comprising a system memory, system mass storage, a keyboard, a screen location-selecting device, and image manipulator and processor means being capable of horizontally shifting said two images separately with respect to each other or simultaneously in congruency in an X-direction and to calculate image shift distances; said X-direction being defined to lie approximately on a plane containing said images and approximately parallel to the line segment connecting the two eyes of said observer;
  (d) a sturdy base to support said video monitor;
  (e) an observing device in working proximity to said video monitor, comprising two parallel optical paths with a left path to direct said left image into the left eye of said observer and a right path to direct said right image into the right eye; each optical path comprising reflector means on one end proximal to said monitor and lens on another end proximal to one of said observer's eyes with said lens encased in an eyepiece; said optical paths being housed and protected by a casing means which is connected to a supporting member; said supporting member being provided with drive means to move said optical paths vertically in a Y-direction, said Y-direction lying approximately parallel to said image plane and perpendicular to said X-direction; said supporting member being further supported by a sturdy base; and (f) two parallel reference lines transversely aligned in the Y-direction with the left reference line lying across the front end, proximal to said left image, of said left optical path and the right reference line lying across the front end, proximal to said right image, of said right optical path; said reference lines being held in place by a fastening means on said casing means.

* * * * *